(12) United States Patent
Olsen

(10) Patent No.: US 7,585,181 B2
(45) Date of Patent: Sep. 8, 2009

(54) DISPOSABLE SURGICAL CONNECTOR

(76) Inventor: Craig Olsen, 120 Knowles Dr., Los Gatos, CA (US) 95032

( * ) Notice: Subject to any disclaimer, the term of this patent is extended or adjusted under 35 U.S.C. 154(b) by 0 days.

(21) Appl. No.: 11/947,572

(22) Filed: Nov. 29, 2007

(65) Prior Publication Data
US 2008/0139033 A1 Jun. 12, 2008

Related U.S. Application Data

(63) Continuation of application No. 11/382,678, filed on May 10, 2006, now Pat. No. 7,351,095.

(51) Int. Cl.
*H01R 13/502* (2006.01)
(52) U.S. Cl. .................. 439/488; 439/909; 439/695
(58) Field of Classification Search .............. 439/488, 439/909, 695, 686, 453, 455; 606/27–52
See application file for complete search history.

(56) References Cited

U.S. PATENT DOCUMENTS

| | | | | |
|---|---|---|---|---|
| 6,010,348 A | * | 1/2000 | Alden | 439/274 |
| 7,241,183 B2 | * | 7/2007 | Wasalaski et al. | 439/686 |
| 2004/0249349 A1 | * | 12/2004 | Wentling | 604/248 |
| 2005/0261582 A1 | * | 11/2005 | Becker et al. | 600/437 |

\* cited by examiner

*Primary Examiner*—Gary F. Paumen
(74) *Attorney, Agent, or Firm*—Peninsula IP Group; Douglas Chaikin

(57) ABSTRACT

Disclosed herein is a disposable surgical connector. The surgical connector includes a first and a second member. Each of the members have compatible guide structure to cause a force fit between the members when the members are slid into place. The first member also includes compatible guide structure for slideably connecting the surgical connector with an electronic or other device. The second member includes a cable connection member which connects the electrical or similar cable to the surgical connector and which secures the cable and its contacts within the surgical connector.

The first member includes a cable connection indicator, which upon complete connection of the surgical connector with the device makes both an audible sound and a distinct tactile feel to give assurance as to the proper fit between both the connector and the device.

10 Claims, 4 Drawing Sheets

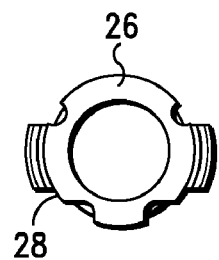
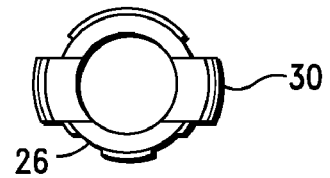
FIG.-8    FIG.-9
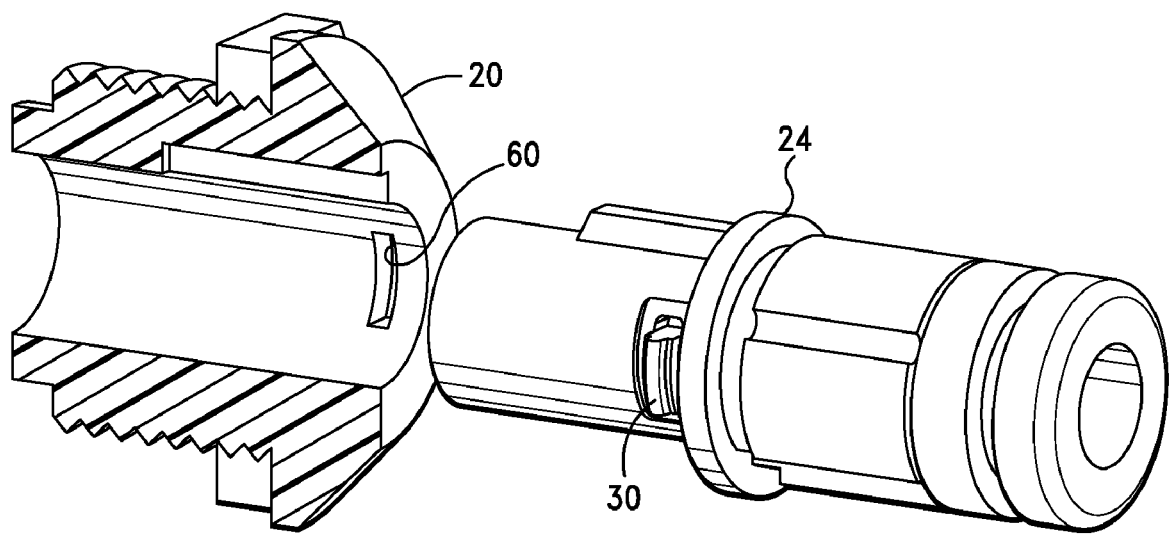
FIG.-10

DISPOSABLE SURGICAL CONNECTOR

CROSS REFERENCE

This application is a continuation application of applicant's earlier filed matter, Ser. No. 11/382,678 filed May 10, 2006, now U.S. Pat. No. 7,351,095.

BACKGROUND OF THE INVENTION

Field of the Invention

This invention relates to connectors used in the medical field. More particularly, this invention relates to connectors which are disposable and which are used to connect a surgical cable from the operating device to a power device such as a computer or other similar device.

In the world of surgical connectors, disposability has become increasingly important. Overwhelmingly, new surgical procedures call for disposing of the cables, connects and all but the most expensive devices in the surgical theater. The spread of infectious diseases is only a small part of the problem. Lawsuits or potential from those who might come into contact with improperly cleaned surgical equipment, such as cables and connectors, make such items disposable even should they be relatively expensive. A single lawsuit is hundreds or even thousands of times more expensive than the cost of simply disposing of the cables and connectors on a routine basis.

Therefore what is needed is a replacement for the relatively inexpensive connectors that provides at least equal reliability while at a fraction of the price of the non-disposable connectors performing precisely the same function. The inventor here has developed such a connector that allows the surgical team, doctors and hospital to dispose of connectors and cables which giving patients and doctors the type of reliability they come to expect and require from non-disposable connectors.

SUMMARY OF THE INVENTION

It is an object of this invention to provide a disposable connector, which provides an indication when there is a proper connection between the connector and the device.

It is an additional object of this invention to provide such a disposable connector, which provides an audible indication of a proper connection between the connector and the device.

It is an additional object of this invention to provide such a disposable connector, which provides a tactile indication of a proper connection between the connector and the device.

In accordance with the above objects and those that will be mentioned and will become apparent below, the disposable surgical connector in accordance with this invention comprising:

a first member including:
   a housing defining a cylindrical body, the body having a guide structure;
   cable connector within the housing
   cable connection indicator member for indicating when the cable is in proper contact with the cable connector; and a second member having an end compatible for mating connection with the cable and the other end compatible for connection with the first member, the second member having a guide structure compatible for connection with the first member guide structure.

In exemplary embodiments of the disposable surgical connector in accordance with this invention, the connection indicator member comprises at least one outwardly projecting tab which is fixed to the first member and upon the cable being slid into proper position with device, the tabs register an audible sound and a distinct tactile feel of being locked in place.

In another exemplary embodiment, the interconnectable elements of the disposable surgical connector in accordance with this invention are slideably connectable and form a force fit to insure proper connection.

It is an advantage of this invention to a provide a surgical connector in accordance with this invention, which provides a relatively inexpensive disposable connector which ensures a proper connection of the connector with the device using both tactile and audible senses.

BRIEF DESCRIPTION OF THE DRAWINGS

For a further understanding of the objects and advantages of the present invention, reference should be had to the following detailed description, taken in conjunction with the accompanying drawing, in which like parts are given like reference numerals and wherein:

FIGS. 8 and 9 are plan views of the connector in accordance with the invention illustrating the cable connection indicator member before and after connection.

FIG. 10 is a partially cut away perspective view of the assembled connector in accordance with the invention prior to connection with a device.

DETAILED DESCRIPTION OF THE INVENTION

Figure 1:
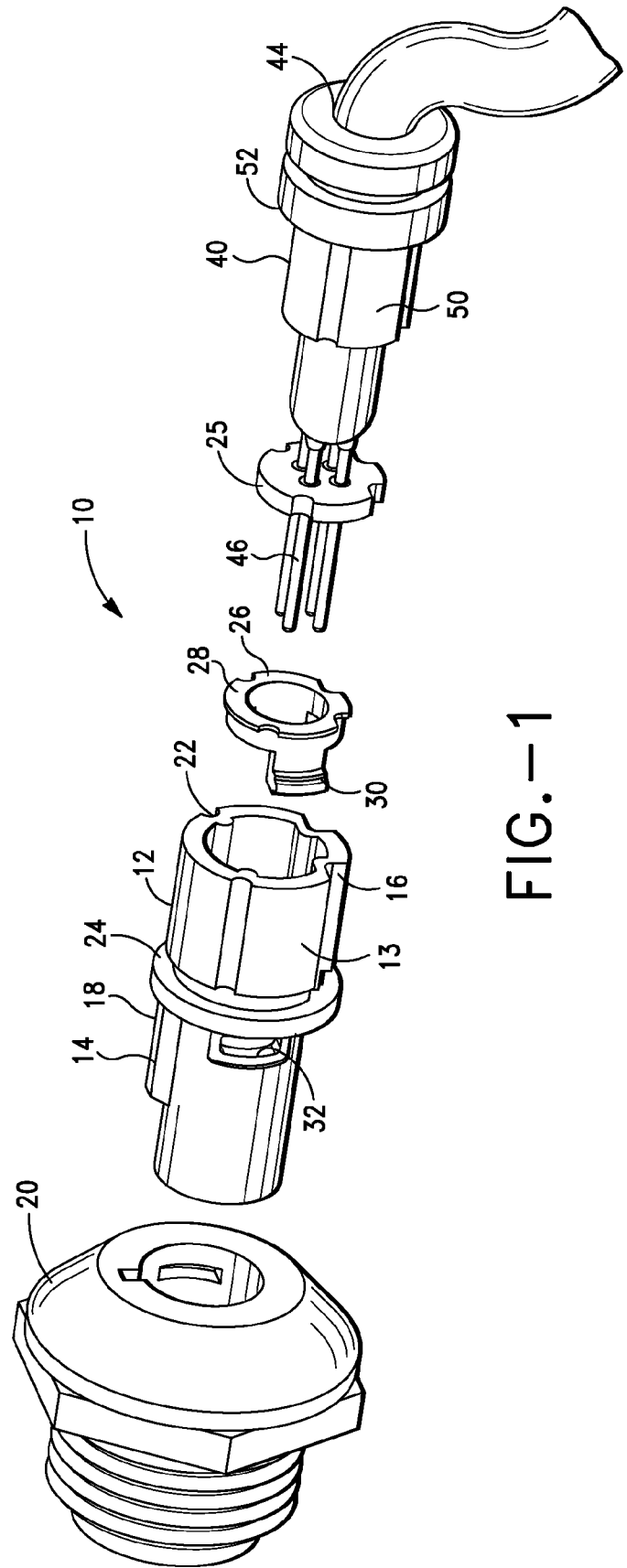
FIG. 1 is an exploded perspective view of the connector in accordance with the invention.

An exemplary embodiment of the disposable surgical connector in accordance with the invention, shown generally by the numeral 10 will now be described with respect to FIG. 1. Typically, the connector 10 is used to connect one end of a cable to a surgical device and the other end to a monitor, such as a computer. After the surgery, the used cable including the connector is discarded.

The connector 10 includes a first member 12. The first member 12 includes a housing 13, which defines a cylindrical body having front and back guide structure 14 and 16, respectively. The front guide structure 14 defines a male key member 18. The male key member 18 is adapted to fit in the female key member of the device 20. The back guide structure 16 includes a series of detents 22 which are sized and shaped for compatible mating engagement with the second member as will be described below.

Additionally, the first member includes a stop 24 between front and back guide structure 14 and 16, respectively. The stop 24 acts to insure a mating fit between the device 20 and the connector 10 and the first and second members.

Figure 3:
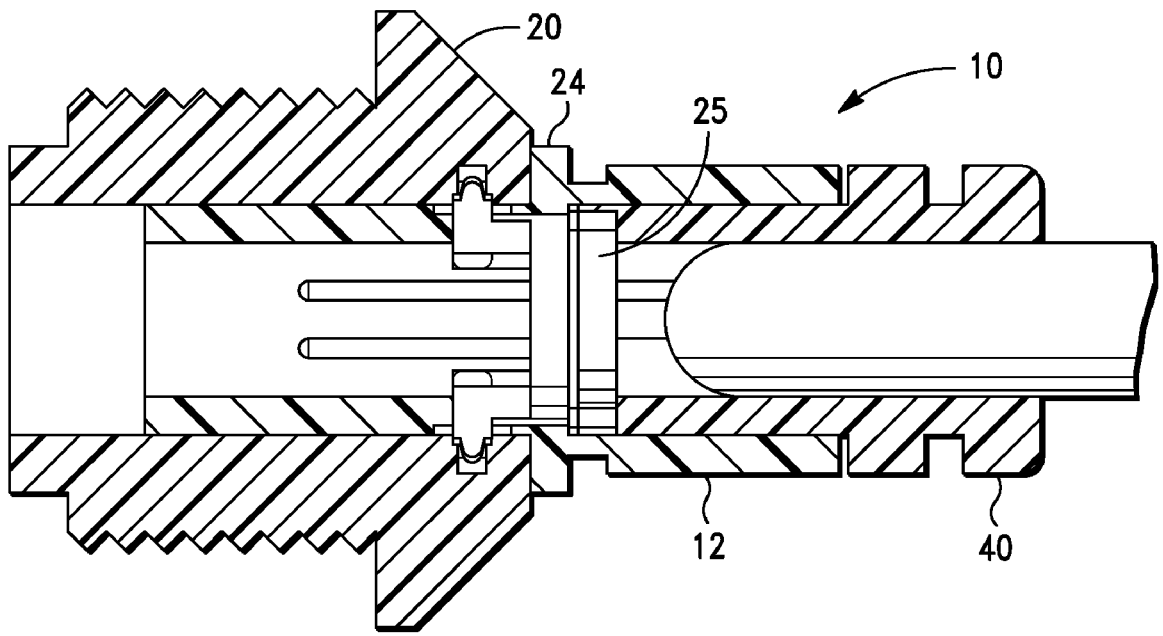
FIG. 3 illustrates the fully assembled connector in accordance with the invention in a cut away plan view.
Figure 4:
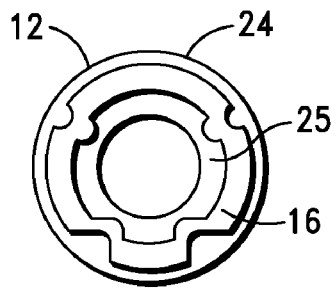
FIG. 4 is a cut away view of the assembled connector in accordance with this invention.

Within the connector first member 12, sits a cable connector 25, as seen more clearly in FIGS. 3 and 4. The cable connector 25 includes a collar with an outer perimeter sized and shaped to fit snugly within the interior diameter of the first member 22. In other words, in the exemplary embodiment shown, the outer perimeter has a series of detents matingly matching the detents of the first member 22.

Also found within the first member interior is the cable connection indicator member 26. The cable connection indicator member 26 defines a collar 28 having an outer perimeter sized and shaped to fit snugly within the interior diameter of the first member 22. Extending form the outer perimeter of the collar 28 is the indicator structure 30. In the exemplary embodiment, the indicator structure comprises a pair of tabs or ears.

Adjacent either side of the front guide structure 14, are a pair of apertures 32. The indicators 30 fit matingly within the apertures. As will be appreciated more fully below, the ears extend fully through the apertures when full and complete contact is made between the connector 10 and the device 20.

Figure 2:
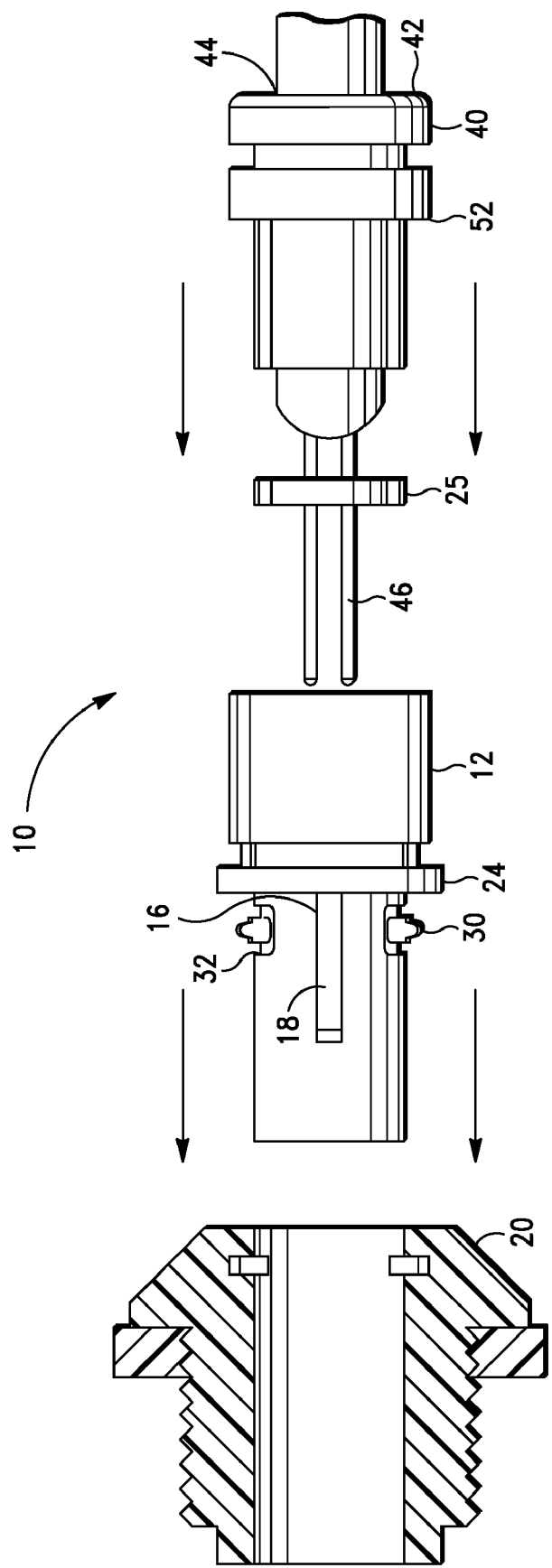
FIG. 2 is an exploded view of the connector in accordance with the invention illustrating the cable connection indicator member in place.

The connector 10 includes a second member as illustrated in FIGS. 1 & 2. One end 42 of the second member 40 has an aperture 44 sized and shaped for compatible fit with the cable. The end of the cable is stripped exposing the leads 46. The leads 46 are threaded compatibly with cable connector 25, which sits within the housing 13.

The second member 40 also has guide structure 50 on the exterior surface, which is matingly compatible with the back guide structure 16 and indicator 26. The second member 40 also has a stop 52, which assures proper seating of the first and second members, 12 and 40, respectively.

The cable connector 25 is pushed within the interior of the first member upon proper connection of the first and second members, 12 and 40, respectively. After proper seating of the first and second members, 12 and 40, respectively, (FIGS. 1 and 2) the connector 10 is then inserted into the device 20 and the indicator 26 makes an audible sound letting the user know that the cable is properly connected to the device 20, both physically and electrically (FIG. 3). The first and second members, 12 and 40, respectively are thus in force fit connection.

With particular reference to FIG. 4, there is shown the back guide structure 16 in side plan view. As shown the stop 24 is concentric with the cable connector 25 and the guide means 16.

Figure 5:
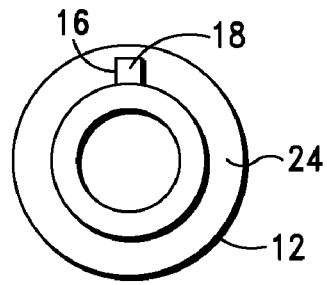
FIG. 5 is an end view of the connector in accordance with the invention prior to insertion into a device.

With particular reference to FIG. 5, there is shown the front guide structure 14 in side plan view. The front guide structure 14 in the form of the male key member 18 in the exemplary embodiment shown in the drawing is concentric with the stop 24.

Figure 6:
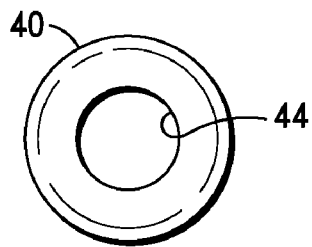
FIG. 6 is an end view of the connector in accordance with the invention prior to insertion with the cable.
Figure 7:
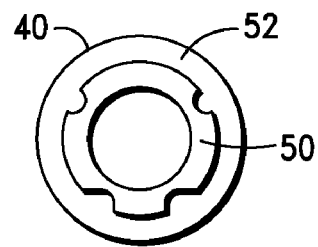
FIG. 7 is an end view of the first member connector in accordance with the invention prior to insertion into the second member.

With particular reference to FIGS. 6 and 7, there is shown the second member 40. In FIG. 6, one end of the second member 40 is shown having aperture 44, while in FIG. 7, the guide structure 50 and the stop 52 and their relationship are shown.

With particular reference to FIGS. 8 and 9, there is shown the cable connection indicator member 26. FIGS. 8 and 9 clearly show the front and back views of indicator member 26. Typically, the indicator 26, including the ears 30 is made from an engineering plastic which provides durability and which makes an audible sound upon being fully engaged with the apertures 32 in the first member 12.

With particular reference to FIG. 10, there is shown the assembled connector 10 in accordance this invention being inserted into the device 20. As is clearly illustrated in FIG. 10, the interior of the device 20 has detents 60 matching the sized and shaped for compatible engagement with the ears 30. As is evident from the shape and size of the ears 30 and the detents 60, when fully engaged, the ears 30 will create a tactile locking feel as well as audible indication of full engagement. It will be appreciated that the ears 30 also serve to secure the connector to the device in proper mating engagement.

While the foregoing detailed description has described one particular embodiment of the connector in accordance with the invention and particularly one embodiment of the indicator which makes an audible and tactile indication that proper engagement between the device and the connector has been achieved. It will be appreciated that other physical representations which are disposable and which give tactile and audible indication of proper connection are possible within the spirit and scope of the invention. Thus, the invention is to be limited only by the claims as set forth below.

The invention claimed is:

1. A disposable surgical connector, adapted for connection on one end to a cable and a port of electrical device on the other end, devoid of O-rings used for a sealing purpose, comprising:
a first member including:
    a housing defining a cylindrical body, the body having a guide structure;
    a cable connector within the housing
    a cable connection indicator member for indicating when the cable is in proper contact with the cable connector, the cable connection indicator member being a separate member from all other elements; and
a second member having an end compatible for mating connection with the cable and the other end compatible for connection with the first member, the second member having a guide structure compatible for connection with the first member guide structure.

2. The disposable connector as set forth in claim 1, wherein the first and the second members are slideably connectable and when in connection form a force fit between the members.

3. The disposable connector as set forth in claim 1, wherein the first member cable connection indicator member comprises at least one outwardly projecting tab, which is fixed to the first member and upon the cable being slid into proper position with the first member, the tabs register an audible sound.

4. The disposable connector as set forth in claim 3, wherein the first member has a pair of opposed slotted openings and the cable connection indicator member tabs fit snugly within the tabs and project outwardly and upon proper cable connection with the cable connector the tabs, an audible sound is made.

5. The disposable connector as set forth in claim 1, wherein the cable connector comprises a multi-pin connector board adapted and aligned for proper mating contact with the cable and the port of the electrical device.

6. The disposable connector as set forth in claim 1, wherein the first member has an exterior and an interior, and wherein the exterior has a guide member for guiding the cable into proper mating connection with the disposable connector, so that an audible sound is made by the cable connector indicator upon proper connection.

7. The disposable connector as set forth in claim 1, wherein the first member has a first end zone and a second end zone; and a middle section flange defining a stop member for properly positioning the connector within the electrical device port; the first end zone have a guide member and the cable indicator member for properly positioning the cable in connection with the disposable connector and the second end zone having exterior adapted for mating connection with the electrical device port and an interior adapted for connection with the second member.

8. The disposable connector as set forth in claim 7, wherein the second member has an interior and an exterior and the exterior adapted for compatible mating connection with the first member interior.

9. The disposable connector as set forth in claim 8, wherein second member have a first end zone adapted for connection to the first member and a second zone adapted for connection with the port of the electrical device.

10. The disposable connector as set forth in claim 9, wherein both the first and second members define hollow cylindrical bodies.

* * * * *